(12) United States Patent
Shigenobu

(10) Patent No.: US 8,431,415 B2
(45) Date of Patent: Apr. 30, 2013

(54) IMMUNOASSAY USING INSOLUBLE CARRIER PARTICLES AND REAGENT THEREFOR

(75) Inventor: Kayoko Shigenobu, Shizuoka (JP)

(73) Assignee: TFB, Inc., Tokyo (JP)

(*) Notice: Subject to any disclaimer, the term of this patent is extended or adjusted under 35 U.S.C. 154(b) by 164 days.

(21) Appl. No.: 12/509,895

(22) Filed: Jul. 27, 2009

(65) Prior Publication Data

US 2009/0286330 A1 Nov. 19, 2009

Related U.S. Application Data

(62) Division of application No. 10/333,785, filed as application No. PCT/JP01/06500 on Jul. 27, 2001, now abandoned.

(30) Foreign Application Priority Data

Jul. 27, 2000 (JP) ................................. 2000-226805

(51) Int. Cl.
*G01N 33/546* (2006.01)

(52) U.S. Cl.
USPC ........... 436/534; 436/518; 436/528; 436/532; 436/536; 436/164; 436/167; 422/68.1; 422/73

(58) Field of Classification Search ................... 436/518, 436/528, 532, 534, 536, 164, 167; 422/68.1, 422/73
See application file for complete search history.

(56) References Cited

U.S. PATENT DOCUMENTS

| | | | |
|---|---|---|---|
| 4,331,862 A | 5/1982 | Ryan | |
| 4,367,279 A | 1/1983 | Herz et al. | |
| 4,395,524 A | 7/1983 | Emmons et al. | |
| 5,162,237 A * | 11/1992 | Messenger et al. | 436/523 |
| 5,470,759 A * | 11/1995 | Sugiyama et al. | 436/541 |
| 5,491,071 A | 2/1996 | Adamczyk et al. | |
| 5,500,348 A | 3/1996 | Nishimura et al. | |
| 5,858,648 A | 1/1999 | Steel et al. | |
| 5,981,296 A | 11/1999 | Stout | |
| 6,174,728 B1 * | 1/2001 | Ben-David et al. | 436/16 |
| 6,670,196 B1 * | 12/2003 | Buechler | 436/518 |
| 2002/0165315 A1 | 11/2002 | Angel et al. | |

FOREIGN PATENT DOCUMENTS

| | | |
|---|---|---|
| EP | 0315866 | 5/1989 |
| JP | 5-80051 | 3/1992 |
| JP | 8-193999 | 7/1996 |
| WO | WO-98/36277 | 8/1998 |

OTHER PUBLICATIONS

Supplementary European Search Report dated May 24, 2007.
European Patent Office Communication dated Jan. 29, 2008.
Molina-Bolivar, JA et al. "Particle Enhanced Immunoassays Stabilized by Hydration Forces: A Comparative Study Between IgG and F(ab')2 Immunoreactivity", Journal of Immunological Methods, 211 (1998), 87.95.
International Search Report PCT/JP01/06500, Jan. 2003.

* cited by examiner

*Primary Examiner* — Melanie Y Brown
(74) *Attorney, Agent, or Firm* — Venable LLP; Robert Kinberg; Nancy J. Axelrod

(57) ABSTRACT

The present invention provides a reagent for an immunoassay comprising insoluble carrier particles which can give the values to be determined with high accuracy and reliability, and can be stored for a long time; an immunoassay using the reagent; and a method for keeping the reagent stable. The present invention provides an immunoassay which comprises carrying out an antigen-antibody reaction using insoluble carrier particles in an aqueous medium comprising a buffer having its buffer capacity in a neutral or alkaline region (except for a carbonate-based buffer) and a carbonic acid compound releasing a bicarbonate ion; a reagent for an immunoassay comprising a buffer having its buffer capacity in a neutral or alkaline region (except for a carbonate-based buffer), a carbonic acid compound releasing bicarbonate ion, and insoluble carrier particles; and a method for keeping the reagent for an immunoassay comprising insoluble carrier particles stable, which comprises allowing insoluble carrier particles to co-exist in an aqueous medium comprising a buffer having its buffer capacity in a neutral or alkaline region (except for a carbonate-based buffer) and a carbonic acid compound releasing a bicarbonate ion.

6 Claims, No Drawings

IMMUNOASSAY USING INSOLUBLE CARRIER PARTICLES AND REAGENT THEREFOR

This application is a divisional of U.S. application Ser. No. 10/333,785, filed Jan. 24, 2003, which is a U.S. National Stage of PCT/JP01/06500, filed Jul. 27, 2001, which claims priority to JP 2000-226805, filed Jul. 27, 2000, which are hereby incorporated by reference.

TECHNICAL FIELD

The present invention relates to an immunoassay using insoluble carrier particles, a reagent for an immunoassay comprising such insoluble carrier particles, and a method for keeping a reagent for an immunoassay comprising such insoluble carrier particles stable.

BACKGROUND ART

In the field of clinical tests, insoluble carrier particles are widely used for immunoassays, which comprise determination of antigens or antibodies in the samples. However, there is a problem that the reproducible values to be determined are not obtained when using a reagent for an immunoassay comprising insoluble carrier particles having been stored for a long time. Thus it is impossible to diagram a calibration curve with the same sensitivity, which results in an error of measurement.

SUMMARY OF THE INVENTION

An object of the present invention is to provide a reagent for an immunoassay comprising insoluble carrier particles that can give the values to be determined with high accuracy and high reliability and can be stored for a long time, an immunoassay using the reagent, and a method for keeping the reagent stable.

The present invention relates to an immunoassay, which comprises carrying out an antigen-antibody reaction using insoluble carrier particles in an aqueous medium comprising a buffer having its buffer capacity in a neutral or alkaline region (except for a carbonate-based buffer) and a carbonic acid compound releasing a bicarbonate ion. According to one embodiment, the carbonic acid compound releasing a bicarbonate ion is an alkali metal compound. According to further embodiments, the concentration of the bicarbonate ion is 0.05 to 500 mmol/L; the concentration of the buffer having its buffer capacity in a neutral or alkaline region is 0.1 to 500 mmol/L; the insoluble carrier particles are those which antibodies reactive with substance to be determined are bound to; the insoluble carrier particles are those which substance to be determined is bound to; the insoluble carrier particles are latex; the immunoassay is a nephelometric immunoassay. Another embodiment is a reagent for an immunoassay comprising a buffer having its buffer capacity in a neutral or alkaline region (except for a carbonate-based buffer), a carbonic acid compound releasing a bicarbonate ion, and insoluble carrier particles. According to further embodiments, the reagent for an immunoassay has the buffer having its buffer capacity in a neutral or alkaline region (except for a carbonate-based buffer), the carbonic acid compound releasing a bicarbonate ion, and insoluble carrier particles are comprised in an aqueous medium; the carbonic acid compound releasing a bicarbonate ion is an alkali metal compound; the concentration of the bicarbonate ion is 0.05 to 500 mmol/L; the concentration of the buffer having its buffer capacity in a neutral or alkaline region is 0.1 to 500 mmol/L; the insoluble carrier particles are those which antibodies reactive with substance to be determined are bound to; the insoluble carrier particles are latex. another embodiment is a method for keeping a reagent for an immunoassay comprising insoluble carrier particles stable, wherein the insoluble carrier particles are comprised in an aqueous medium comprising a buffer having its buffer capacity in a neutral or alkaline region (except for a carbonate-based buffer) and a carbonic acid compound releasing a bicarbonate ion. According to further embodiments, the carbonic acid compound releasing a bicarbonate ion is an alkali metal compound; the concentration of the bicarbonate ion is 0.05 to 500 mmol/L; the the concentration of the buffer having its buffer capacity in a neutral or alkaline region is 0.1 to 500 mmol/L; the insoluble carrier particles are those which antibodies reactive with substance to be determined are bound to; the insoluble carrier particles are latex.

BEST MODE OF CARRYING OUT THE INVENTION

As a buffer having its buffer capacity in a neutral or alkaline region (except for a carbonate-based buffer) for the present invention, there is no specific limitation as long as the buffer has its buffer capacity at over pH 7, and the buffer having its buffer capacity at pH 7 to 12 is preferable, and the buffer having its buffer capacity at pH 8 to 11 is more preferable. Examples include an organic amine buffer, a Good's buffer, a buffer for biochemical use, and the like.

Examples of the above-mentioned buffer for biochemical use include imidazole buffer, sodium dihydrogenphosphate-disodium hydrogenphosphate buffer, citrate-disodium hydrogenphosphate buffer, hydrochloric acid-veronal sodium-sodium acetate buffer, potassium dihydrogenphosphate-disodium hydrogenphosphate buffer, potassium dihydrogenphosphate-borax buffer, potassium dihydrogenphosphate-sodium hydroxide buffer, hydrochloric acid-collidine buffer, hydrocholoric acid-veronal sodium buffer, hydrochloric acid-tris(hydroxymethyl)aminomethane buffer, hydrochloric acid-borax buffer, borate-sodium carbonate buffer, borate-borax buffer, hydrochloric acid-aminomethylpropanediol buffer, ammonium chloride-ammonia buffer, glycine-sodium hydroxide buffer, borate-sodium hydroxide buffer, hydrochloric acid-dimethylglycine sodium buffer, borax-sodium hydroxide buffer, borax-sodium carbonate buffer, glycine-sodium chloride-hydrochloric acid buffer, disodium hydrogen citrate-hydrochloric acid buffer, disodium hydrogen citrate-sodium hydroxide buffer, borax-sodium chloride buffer, veronal sodium-sodium acetate-hydrochloric acid buffer, borate-potassium chloride-sodium hydroxide buffer, Tris-maleate buffer, maleate buffer, veronal-acetate buffer, veronal buffer, Michaelis buffer, Clark-Lubs' buffer, Atkins-Pantin buffer, Paritish buffer, Kolthoff's buffer, MacIlvaine buffer, Hasting-Sendroi buffer, Britton-Robinson buffer, Sørensen buffer.

Examples of the above-mentioned organic amine buffer include diethanolamine buffer, 2-ethylaminoethanol buffer, 2-amino-2-methyl-1-propanol buffer, N-methyl-D-glucamine and the like.

Examples of the above-mentioned Good's buffer include MES (2-morpholinoethanesulfonic acid) buffer, bis-tris[bis(2-hydroxyethyl)imino tris(hydroxymethyl)methane] buffer, ADA [N-(2-acetamido)iminodiacetic acid] buffer, PIPES [piperazine-N,N'-bis(2-ethanesulfonic acid)] buffer, ACES {2-[N-(2-acetamido)amino]ethanesulfonic acid} buffer, MOPSO (3-morpholino-2-hydroxypropanesulfonic acid) buffer, BES {2-[N,N-bis(2-hydroxyethyl)amino]ethanesulfonic acid} buffer, MOPS (3-morpholinopropanesulfonic acid) buffer, TES <2-{N-[tris(hydroxymethyl)methyl]amino}ethanesulfonic acid> buffer, HEPES [N-(2-hydroxyethyl)-N'-(2-sulfoethyl)piperazine] buffer, DIPSO {3-[N,N-bis(2-hydroxyethyl)amino]-2-hydroxypropanesulfonic acid} buffer, TAPSO <2-hydroxy-3-{[N-tris(hydroxymethyl) methyl]amino}propanesulfonic acid> buffer, POPSO [piperazine-N,N'-bis(2-hydroxy-3-propanesulfonic acid)] buffer, HEPPSO [N-(2-hydroxyethyl)-N'-(2-hydroxy-3-sulfopropyl)piperazine] buffer, EPPS [N-(2-hydroxyethyl)-N'-(3-sulfopropyl)piperazine] buffer, tricine {N-[tris(hydroxymethyl)methyl]glycine} buffer, bicine[N,N-bis(2-hydroxyethyl)glycine] buffer, TAPS {3-[N-tris(hydroxymethyl)methyl]aminopropanesulfonic acid} buffer, CHES [2-(N-cyclohexylamino)ethanesulfonic acid] buffer, CAPSO [3-(N-cyclohexylamino)-2-hydroxypropanesulfonic acid] buffer, CAPS [3-(N-cyclohexylamino)propanesulfonic acid] buffer, and the like.

The buffer having its buffer capacity in a neutral or alkaline region in the present invention is a buffer other than a carbonate-based buffer. The carbonate-based buffer mentioned here represents a buffer based on a carbonate, and examples of the carbonate-based buffer include sodium carbonate-sodium bicarbonate buffer, potassium carbonate-potassium bicarbonate buffer and the like.

Furthermore, there is no specific limitation for the concentration of the buffer having its buffer capacity in a neutral or alkaline region according to the present invention. A concentration of 0.1 mmol/L to 500 mmol/L is preferable, a concentration of 1 mmol/L to 100 mmol/L is more preferable, and a concentration of 5 mmol/L to 50 mmol/L is most preferable.

There is no specific limitation for the carbonic acid compound releasing a bicarbonate ion in the present invention, as long as the compound is a compound releasing a bicarbonate ion, and the carbonic acid releasing a bicarbonate-ion is exemplified by an alkali metal compound or an alkali earth metal compound and the like. Examples of the alkali metal compound and the alkali earth metal compound include sodium bicarbonate, potassium bicarbonate, magnesium bicarbonate, calcium bicarbonate, and the like. The alkali metal compounds such as sodium bicarbonate and potassium bicarbonate are preferably used.

Furthermore, there is no specific limitation for the concentration of the carbonic acid compound releasing a bicarbonate ion. A concentration, of 0.05 to 500 mmol/L is preferable, a concentration of 0.1 mmol/L to 100 mmol/L is more preferable, and a concentration of 1 to 50 mmol/L is most preferable.

As an aqueous medium for the present invention, water, especially purified water is exemplified, and the aqueous medium may comprise, if necessary, enzymes, coenzymes, soluble salts such as sodium chloride, detergents such as Triton X-100 and Tween 20, stabilizing agents, antiseptics such as sodium azide, and the like.

The insoluble carrier particles used in the present invention is not specifically limited, and examples of the insoluble carrier particles include microparticles of organic polymers, microparticles of inorganic oxides, microparticles in which surface of the organic polymers or the inorganic oxides was treated with organic matters, and the like. There is no specific limitation for the materials of insoluble carrier particles, and the preferred are the materials that enable the insoluble carrier particles to be suspended uniformly in the reaction solution.

Furthermore, there is no limitation for the particle diameter of the insoluble carrier particles employable in the present invention, and the particles with the diameter of 0.4 to 0.8 im are preferable. As more preferable insoluble carrier particles, latex such as polystyrene latex are exemplified. As a material of the latex, styrene latex such as polystyrene latex, acrylic acid latex and the like are exemplified. Additionally, polystyrene latex, prepared by co-polymerization of a monomer of acrylic acid, a monomer having sulfonic acid and the like as a monomer component to give electric charges, can be used preferably.

There is no specific limitation for the concentration of insoluble carrier particles in the reaction solution or in the reagent, and the concentration of 0.005 to 2% by weight in the solution is preferable.

There is no specific limitation for substance to be determined in an immunoassay according to the present invention, and examples of the substance include antigens such as ferritin and hemoglobin A1c (hereinafter referred to as HbA1c), antibodies to these antigens and the like.

In the present invention, "an antigen-antibody reaction using insoluble carrier particles" refers to an antigen-antibody reaction using insoluble carrier particles as a solid phase. As insoluble carrier particles as a solid phase, those which substance to be determined or antibodies reactive with the substance to be determined are carried by (bound to) in advance as well as those which neither substance to be determined nor antibodies reactive with the substance to be determined are substantially carried by (bound to) are used. The immunoassay employable in the present invention is not specifically limited, as long as the immunoassay comprises an antigen-antibody reaction using insoluble carrier particles in an aqueous medium, and for example, a nephelometric immunoassay is mentioned.

The immunoassay in the present invention comprises the following steps: 1) the step of adding the above-mentioned insoluble carrier particles to an aqueous medium comprising a buffer having its buffer capacity in a neutral or alkaline region (except for a carbonate-based buffer) and a carbonic acid compound releasing a bicarbonate ion to give a suspension; 2) the step of reacting the suspension comprising the insoluble carrier particles with the sample comprising substance to be determined; 3) the step of measuring agglutination of insoluble carrier particles originated from the reaction.

In case insoluble carrier particles, which neither substance to be determined nor antibodies to the substance to be determined are carried by (bound to), are used as insoluble carrier particles, the step of reacting the suspension comprising the insoluble carrier particles with the sample comprising the substance to be determined is followed by the step of adding the reagent comprising antibodies reactive with the substance to be determined thereto.

There is no specific limitation for a reagent for an immunoassay according to the present invention as long as the reagent comprises a buffer having its buffer capacity in a neutral or alkaline region (except for a carbonate-based buffer), a carbonic acid compound releasing a bicarbonate ion, and insoluble carrier particles. The buffer having its buffer capacity in a neutral or alkaline region (except for a carbonate-based buffer), the carbonic acid compound releasing a bicarbonate ion, and insoluble carrier particles may be comprised in an aqueous medium. As the buffer having its buffer capacity in a neutral or alkaline region (except for a carbonate-based buffer), the carbonic acid compound releasing a bicarbonate ion, the insoluble carrier particles and the aqueous medium, those as mentioned above are exemplified, respectively. The reagent according to the present invention may comprise, if necessary, enzymes, coenzymes, soluble salts such as sodium chloride, detergents such as Triton X-100 and Tween 20, stabilizing agents, antiseptics such as sodium azide, and the like.

A reagent for an immunoassay according to the present invention may be stored and used in the form of a kit. Examples of a form of a kit include a kit consisted of two reagents, a kit consisted of three reagents, and the like. Examples of a kit consisted of two reagents according to the present invention include: a kit consisted of a first reagent and a second reagent, wherein the first reagent comprises in an aqueous medium a buffer having its buffer capacity in a neutral or alkaline region (except for a carbonate-based buffer), and a carbonic acid compound releasing a bicarbonate ion, and the second reagent comprises in an aqueous medium insoluble carrier particles which the antibodies reactive with the substance to be determined are bound to, a buffer having its buffer capacity in a neutral or alkaline region (except for a carbonate-based buffer), and a carbonic acid compound releasing a bicarbonate ion; a kit consisted of a first reagent and a second reagent, wherein the first reagent comprises insoluble carrier particles which neither the substance to be determined nor the antibodies to the substance are not substantially carried by (bound to), a buffer having its buffer capacity in a neutral or alkaline region (except for a carbonate-based buffer), and a carbonic acid compound releasing a bicarbonate ion, and the second reagent comprises in an aqueous medium the antibodies reactive with the substance to be determined.

A method for keeping a reagent for an immunoassay comprising insoluble carrier particles stable according to the present invention is not specifically limited, as long as the method comprises allowing insoluble carrier particles to present in an aqueous medium comprising a buffer having its buffer capacity in a neutral or alkaline region (except for a carbonate-based buffer) and a carbonic acid compound releasing a bicarbonate ion. As the buffer having its buffer capacity in a neutral or alkaline region (except for a carbonate-based buffer), the carbonic acid compound releasing a bicarbonate ion, the insoluble carrier particles and the aqueous medium, those as mentioned above may be used, respectively. In the aqueous medium, the following may be comprised, if necessary: enzymes, coenzymes, soluble salts such as sodium chloride, detergents such as Triton X-100 and Tween 20, stabilizing agents, antiseptics such as sodium azide, and the like.

A condition for storage of a reagent for an immunoassay according to the present invention is not specifically limited, and for example, the reagent can be stored at 0 to 30.degree. C., preferably at 0 to 5.degree. C. The method for keeping a reagent for an immunoassay comprising insoluble carrier particles stable according to the present invention is more effective for keeping the reagent stable when the reagent is stored under an unsealed condition where deterioration of the reagent is considered to occur easily.

The present invention will be described in detail by the following examples, while the scope of the invention will not be limited to these examples.

Example 1

The following Reagent R1 and Reagent R2 were prepared.

| Reagent R1 | |
|---|---|
| bicine buffer (DOJINDO Laboratories, pH 8.4) | 3.26 g/L |
| Triton X-100 (Sigma) | 0.1 g/L |
| sodium chloride (Wako Pure Chemical Industries, Ltd.) | 17.5 g/L |
| sodium azide (Kanto Chemical Co., Inc.) | 0.01 g/L |
| sodium bicarbonate (Kanto Chemical Co., Inc.) | 0.2 g/L |

| Reagent R2 (a suspension of the latex carrying the antibodies thereon) | |
|---|---|
| imidazole buffer (Nacalai Tesque, Inc., pH 8.4) | 0.68 g/L |
| Triton X-100 (Sigma) | 0.15 g/L |
| sodium bicarbonate (Kanto Chemical Co., Inc.) | 0.2 g/L |
| the latex carrying the antibodies thereon (prepared in reference example) | 0.1% by weight |

Example 2

The following Reagent R1 and Reagent R2 were prepared.

| Reagent R1 | |
|---|---|
| bicine buffer (DOJINDO Laboratories, pH 8.4) | 3.26 g/L |
| Triton X-100 (Sigma) | 0.1 g/L |
| sodium chloride (Wako Pure Chemical Industries, Ltd.) | 17.5 g/L |
| sodium azide (Kanto Chemical Co., Inc.) | 0.01 g/L |
| sodium bicarbonate (Kanto Chemical Co., Inc.) | 0.4 g/L |

| Reagent R2 (a suspension of the latex carrying the antibodies thereon) | |
|---|---|
| imidazole buffer (Nacalai Tesque, Inc., pH 8.4) | 0.68 g/L |
| Triton X-100 (Sigma) | 0.15 g/L |
| sodium bicarbonate (Kanto Chemical Co., Inc.) | 0.4 g/L |
| the latex carrying the antibodies thereon (prepared in reference example) | 0.1% by weight |

Example 3

The following Reagent R1 and Reagent R2 were prepared.

| Reagent R1 | |
|---|---|
| bicine buffer (DOJINDO Laboratories, pH 8.4) | 3.26 g/L |
| Triton X-100 (Sigma) | 0.1 g/L |
| sodium chloride (Wako Pure Chemical Industries, Ltd.) | 17.5 g/L |
| sodium azide (Kanto Chemical Co., Inc.) | 0.01 g/L |
| sodium bicarbonate (Kanto Chemical Co., Inc.) | 0.6 g/L |

| Reagent R2 (a suspension of the latex carrying the antibodies thereon) | |
|---|---|
| imidazole buffer (Nacalai Tesque, Inc., pH 8.4) | 0.68 g/L |
| Triton X-100 (Sigma) | 0.15 g/L |
| sodium bicarbonate (Kanto Chemical Co., Inc.) | 0.6 g/L |
| the latex carrying the antibodies thereon (prepared in reference example) | 0.1% by weight |

Comparative Example 1

The following Reagent R1 and Reagent R2 were prepared.

| Reagent R1 | |
|---|---|
| bicine buffer (DOJINDO Laboratories, pH 8.4) | 3.26 g/L |
| Triton X-100 (Sigma) | 0.1 g/L |
| sodium chloride (Wako Pure Chemical Industries, Ltd.) | 17.5 g/L |
| sodium azide (Kanto Chemical Co., Inc.) | 0.01 g/L |

| Reagent R2 | |
|---|---|
| (a suspension of the latex carrying the antibodies thereon) | |
| imidazole buffer (Nacalai Tesque, Inc., pH 8.4) | 0.68 g/L |
| Triton X-100 (Sigma) | 0.15 g/L |
| the latex carrying the antibodies thereon (prepared in reference example) | 0.1% by weight |

Example 4

The following Reagent R1 and Reagent R2 were prepared.

| Reagent R1 (a suspension of the latex) | |
|---|---|
| bicine buffer (DOJINDO Laboratories, pH 7.8) | 3.26 g/L |
| sodium azide (Kanto Chemical Co., Inc.) | 0.1 g/L |
| sodium bicarbonate (Kanto Chemical Co., Inc.) | 0.1 g/L |
| the latex (particle diameter: 0.0775 μm, SEKISUI Chemical Co., Ltd.) | 0.033% by weight |

| Reagent R2 | |
|---|---|
| bicine buffer (DOJINDO Laboratories, pH 7.0) | 3.26 g/L |
| sodium chloride (Wako Pure Chemical Industries, Ltd.) | 15.0 g/L |
| Tween 20 (Wako Pure Chemical Industries, Ltd.) | 2.0 g/L |
| sodium azide (Kanto Chemical Co., Inc.) | 0.1 g/L |
| anti-human HbA1c mouse monoclonal antibody | 0.025 g (in terms of IgG)/L |
| anti-mouse IgG goat polyclonal antibody (Wako Pure Chemical Industries, Ltd.) | 0.04 g (in terms of IgG)/L |

Example 5

The following Reagent R1 and Reagent R2 were prepared.

| Reagent R1 (a suspension of the latex) | |
|---|---|
| bicine buffer (DOJINDO Laboratories, pH 7.8) | 3.26 g/L |
| sodium azide (Kanto Chemical Co., Inc.) | 0.1 g/L |
| sodium bicarbonate (Kanto Chemical Co., Inc.) | 0.2 g/L |
| the latex (particle diameter: 0.0775 μm, SEKISUI Chemical Co., Ltd.) | 0.033% by weight |

| Reagent R2 | |
|---|---|
| bicine buffer (DOJINDO Laboratories, pH 7.0) | 3.26 g/L |
| sodium chloride (Wako Pure Chemical Industries, Ltd.) | 15.0 g/L |
| Tween 20 (Wako Pure Chemical Industries, Ltd.) | 2.0 g/L |
| sodium azide (Kanto Chemical Co., Inc.) | 0.1 g/L |
| anti-human HbA1c mouse monoclonal antibody | 0.025 g (in terms of IgG)/L |
| anti-mouse IgG goat polyclonal antibody (Wako Pure Chemical Industries, Ltd.) | 0.04 g (in terms of IgG)/L |

Example 6

The following Reagent R1 and Reagent R2 were prepared.

| Reagent R1 (a suspension of the latex) | |
|---|---|
| bicine buffer (DOJINDO Laboratories, pH 8.4) | 3.26 g/L |
| sodium azide (Kanto Chemical Co., Inc.) | 0.1 g/L |
| sodium bicarbonate (Kanto Chemical Co., Inc.) | 0.2 g/L |
| the latex (particle diameter: 0.0775 μm, SEKISUI Chemical Co., Ltd.) | 0.033% by weight |

| Reagent R2 | |
|---|---|
| bicine buffer (DOJINDO Laboratories, pH 7.0) | 3.26 g/L |
| sodium chloride (Wako Pure Chemical Industries, Ltd.) | 15.0 g/L |
| Tween 20 (Wako Pure Chemical Industries, Ltd.) | 2.0 g/L |
| sodium azide (Kanto Chemical Co., Inc.) | 0.1 g/L |
| anti-human HbA1c mouse monoclonal antibody | 0.025 g (in terms of IgG)/L |
| anti-mouse IgG goat polyclonal antibody (Wako Pure Chemical Industries, Ltd.) | 0.04 g (in terms of IgG)/L |

Example 7

The following Reagent R1 and Reagent R2 were prepared.

| Reagent R1 (a suspension of the latex) | |
|---|---|
| bicine buffer (DOJINDO Laboratories, pH 8.4) | 3.26 g/L |
| sodium azide (Kanto Chemical Co., Inc.) | 0.1 g/L |
| sodium bicarbonate (Kanto Chemical Co., Inc.) | 0.3 g/L |
| the latex (particle diameter: 0.0775 μm, SEKISUI Chemical Co., Ltd.) | 0.033% by weight |

| Reagent R2 | |
|---|---|
| bicine buffer (DOJINDO Laboratories, pH 7.0) | 3.26 g/L |
| sodium chloride (Wako Pure Chemical Industries, Ltd.) | 15.0 g/L |
| Tween 20 (Wako Pure Chemical Industries, Ltd.) | 2.0 g/L |
| sodium azide (Kanto Chemical Co., Inc.) | 0.1 g/L |
| anti-human HbA1c mouse monoclonal antibody | 0.025 g (in terms of IgG)/L |
| anti-mouse IgG goat polyclonal antibody (Wako Pure Chemical Industries, Ltd.) | 0.04 g (in terms of IgG)/L |

Comparative Example 2

The following Reagent R1 and Reagent R2 were prepared.

| Reagent R1 (a suspension of the latex) | |
|---|---|
| bicine buffer (DOJINDO Laboratories, pH 7.8) | 3.26 g/L |
| sodium azide (Kanto Chemical Co., Inc.) | 0.1 g/L |
| the latex (particle diameter: 0.0775 μm, SEKISUI Chemical Co., Ltd.) | 0.033% by weight |

| Reagent R2 | |
|---|---|
| bicine buffer (DOJINDO Laboratories, pH 7.0) | 3.26 g/L |
| sodium chloride (Wako Pure Chemical Industries, Ltd.) | 15.0 g/L |
| Tween 20 (Wako Pure Chemical Industries, Ltd.) | 2.0 g/L |
| sodium azide (Kanto Chemical Co., Inc.) | 0.1 g/L |
| anti-human HbA1c mouse monoclonal antibody | 0.025 g (in terms of IgG)/L |
| anti-mouse IgG goat polyclonal antibody (Wako Pure Chemical Industries, Ltd.) | 0.04 g (in terms of IgG)/L |

Comparative Example 3

The following Reagent R1 and Reagent R2 were prepared.

| Reagent R1 (a suspension of the latex) | |
|---|---|
| bicine buffer (DOJINDO Laboratories, pH 8.4) | 3.26 g/L |
| sodium azide (Kanto Chemical Co., Inc.) | 0.1 g/L |
| the latex (particle diameter: 0.0775 μm, SEKISUI Chemical Co., Ltd.) | 0.033% by weight |

| Reagent R2 | |
|---|---|
| bicine buffer (DOJINDO Laboratories, pH 7.0) | 3.26 g/L |
| sodium chloride (Wako Pure Chemical Industries, Ltd.) | 15.0 g/L |
| Tween 20 (Wako Pure Chemical Industries, Ltd.) | 2.0 g/L |
| sodium azide (Kanto Chemical Co., Inc.) | 0.1 g/L |
| anti-human HbA1c mouse monoclonal antibody | 0.025 g (in terms of IgG)/L |
| anti-mouse IgG goat polyclonal antibody (Wako Pure Chemical Industries, Ltd.) | 0.04 g (in terms of IgG)/L |

Reference Example

Preparation of the Latex Carrying the Antibody Thereon

Latex was diluted by adding 9 equivalents of 1/60 mol/L PBS solution (adjusted to pH 7.4 with 1 mol/L hydrochloric acid or sodium hydroxide solution) to one equivalent of 10% suspension of polystyrene latex (JSR) having the average particle diameter of 0.31 ìm to give the 1% latex solution. The anti-human ferritin antibody (polyclonal antibody, Kyowa Medex Co., LTD.) was diluted with a 1/60 mol/L PBS solution to give the antibody solution comprising the protein at a concentration of 50 ìg/mL, with which the antibody was carried by latex. With stirring the 1% latex suspension (600 ìL) with a magnetic stirrer at 25.degree. C. in an incubator, the antibody solution (1200 ìL) prepared above was quickly added to the suspension, and the mixture was stirred at 25.degree. C. for two hours. Then, blocking solution 1 (3 mL) prepared as described below was added thereto, and the mixture was further stirred at 25.degree. C. for two hours. The mixture was then centrifuged at 15,000 rpm at 4.degree. C. for one hour. Subsequently, the precipitate thus obtained was rinsed by adding blocking solution 1 (4 mL) and then by centrifuging the mixture under a similar condition. After rinsing three times, the precipitate obtained was used as the latex carrying the antibody thereon.

Blocking Solution 1

BSA (bovine serum albumin) (6 g), Triton X-100 (Sigma) (0.15 g) were added to an aqueous solution of imidazole buffer (0.68 g). Then, the pH was adjusted to 7.4 by addition of 1 mol/L hydrochloric acid or sodium hydroxide solution while measuring the pH level at 20.degree. C. The solution was made 1000 mL in total by addition of distilled water to give blocking solution 1.

Test Example 1

The concentration of ferritin in the serum samples was determined in the manner described below, by using each Reagent R1 and each Reagent R2 prepared in Examples 1 to 3 and Comparative Example 1. Each Reagent R1 and each Reagent R2 just after preparation were stored in bottles for autoanalyzer under a sealed condition at 4.degree. C., and after three days, unsealed. Then, the concentration of ferritin was determined using each of the reagent just after unsealing (reagent just after unsealing), the reagent further stored under an unsealed condition at 4.degree. C. for 14 days after unsealing (reagent stored for 14 days after unsealing), and the reagent further stored under an unsealed condition at 4.degree. C. for 28 days after unsealing (reagent stored for 28 days after unsealing).

Preparation of a Serum Sample

Human blood was collected with a blood tube (VENJECT Glass Vacuum Tubes; TERUMO Corp.) and was left for two hours to give a supernatant fluid (serum), which was made a serum sample. The sample was frozen to store at −20.degree. C., and the frozen sample was melted just before use.

Determination of the Concentration of Ferritin Using Reagent R1 and Reagent R2

A calibration curve was diagramed by using Reagent R1 and Reagent R2 just after unsealing, along with ferritin standard solutions with concentrations of 10.9, 21.9, 43.8, 87.5 and 175 ng/mL, respectively, which were prepared by using a ferritin standard (Scripps Laboratories Inc.).

Determination of the concentration of a serum sample was carried out as follows. Serum sample (10 ìL) was added to Reagent R1 (140 ìL) and the reaction was allowed to occur at 37.degree. C. for 6 minutes. Then, Reagent R2 (150 ìL) was added thereto, and the reaction was allowed to occur at 37.degree. C. for 13 minutes. Then, changes in absorbance were measured by the 2 point-end method (photometric points: 21 and 39) with the main-wavelength of 750 nm and the sub-wavelength of 800 nm, wherein the measurement was carried out on Hitachi autoanalyzer 7170.

The results of the determination of the concentrations of ferritin using the reagents prepared in Examples 1 to 3 and Comparative Example 1 are shown in Table 1.

TABLE 1

| days after unsealing of reagents (days) | Example 1 | Example 2 | Example 3 | Comparative Example 1 |
|---|---|---|---|---|
| 0 | 61 | 62 | 62 | 62 |
| 14 | 66 | 62 | 60 | 74 |
| 28 | 69 | 62 | 57 | 83 |

As shown in Table 1, in the determination of ferritin concentration using the reagent of Comparative Example 1 consisting of Reagents R1 and R2, neither of which comprises no sodium bicarbonate, the values to be determined of ferritin concentration changed significantly with the passage of days after unsealing of the reagent, while in the determination of ferritin concentration using the reagents of Examples 1 to 3 consisting of each Reagent R1 and each Reagent R2, both of which comprise sodium bicarbonate, the values to be determined of ferritin concentration did not change so much even with the passage of days after unsealing of the reagent.

Test Example 2

The rate of HbA1c to hemoglobin in a sample (hereinafter referred to as a concentration of HbA1c) was determined in the manner described below, by using each Reagent R1 and each Reagent R2, prepared respectively in Examples 4 to 5 and Comparative Example 2, and Examples 6 to 7 and Comparative Example 3. As Reagent R1 in the determination of the concentration of HbA1c, the following reagents were used: the reagent just after unsealing of each Reagent 1, which was stored at 4.degree. C. for three days in bottles for autoanalyzer under a sealed condition just after preparation (reagent just after unsealing); the reagent stored at 4.degree. C. for 14 days under an unsealed condition after unsealing of each Reagent R1, which was stored at 4.degree. C. for three days in bottles for autoanalyzer under a sealed condition just after preparation (reagent stored for 14 days after unsealing); and the reagent stored at 4.degree. C. for 28 days under an unsealed condition after unsealing of each Reagent R1, which was stored at 4.degree. C. for three days in bottles for autoanalyzer under a sealed condition just after preparation (reagent stored for 28 days after unsealing). As Reagent R2 in the determination of the concentration of HbA1c, the following reagent was used: the reagent just after unsealing of each Reagent R2, which was stored at 4.degree. C. for three days in bottles for autoanalyzer under a sealed condition just after preparation.

Preparation of the Samples

Human blood was collected with an EDTA blood tube (VENOJEC Glass Vacuum Tubes; TERUMO Corp.). The blood was left for two hours to give the precipitated hemocyte layer. The hemocyte layer (10 μL) was diluted with purified water (1 mL), and the mixture was frozen to store at −20.degree. C., and the frozen sample was melted just before use.

Determination of the Concentration of HbA1c Using Reagent R1 and Reagent R2

A calibration curve was diagramed using Reagent R1 and Reagent R2 just after unsealing, along with the standard samples with the values of HbA1c (=the concentration of HbA1c) of 0.0%, 4.2%, 7.7%, 11.3% and 14.8%, respectively, which were determined by an autoanalyzer of glycohemoglobin, HLC-723 GHbV (Tohso Corp.).

Determination of the concentration of HbA1c was carried out as follows. The sample (3.2 μL) prepared as mentioned above was added to Reagent R1 (240 iL), and the reaction was allowed to occur at 37.degree. C. for 5 minutes. Then, Reagent R2 (80 iL) was added thereto, and the reaction was allowed to occur at 37.degree. C. for 5 minutes. Then, changes in absorbance were measured by the 2 point-end method (photometric points: 16 and 34) with the main-wavelength of 450 nm and the sub-wavelength of 800 nm, wherein the measurement was carried out on Hitachi autoanalyser 7170.

The results of the determination of the concentration of HbA1c (%) by using the reagents prepared in Examples 4 to 5 and Comparative Example 2 are shown in Table 2, and the results of the determination of the concentration of HbA1c (%) by using the reagents prepared in Examples 6 to 7 and Comparative Example 3 are shown in Table 3.

TABLE 2

| Days after unsealing of Reagent R1 (days) | Example 4 | Example 5 | Comparative Example 2 |
|---|---|---|---|
| 0 | 6.0 | 6.1 | 6.0 |
| 14 | 6.0 | 6.0 | 6.4 |
| 28 | 6.1 | 5.8 | 6.8 |

TABLE 3

| Days after unsealing of Reagent R1 (days) | Example 6 | Example 7 | Comparative Example 3 |
|---|---|---|---|
| 0 | 6.0 | 6.1 | 6.1 |
| 14 | 6.4 | 6.1 | 6.8 |
| 28 | 6.5 | 6.1 | 7.5 |

As shown in Tables 2 and 3, in the determination of the concentration of HbA1c using the reagents prepared in Comparative Example 2 and 3, which comprise Reagent R1 comprising no sodium bicarbonate, the values to be determined of the concentration of HbA1c changed significantly with the passage of days after unsealing of the reagents, while in the determination of the concentration HbA1c using the reagents prepared in Examples 4 to 7, which comprise Reagent R1 comprising sodium bicarbonate, the values to be determined of the concentration of HbA1c did not change so much even with the passage of days after unsealing of the reagents.

INDUSTRIAL APPLICABILITY

According to the present invention, the non-specific agglutination of the insoluble carrier particles is suppressed, which makes specific determination possible, and an immunoassay with high accuracy and reliability can be provided. The present invention further provides a reagent for an immunoassay, in which non-specific agglutination is suppressed even after a long storage. The present invention furthermore provides a method for keeping a reagent for an immunoassay comprising insoluble carrier particles stable even after a storage for a long time.

The invention claimed is:

1. A nephelometric immunoassay, which comprises the steps of:
   1) preparing a suspension by adding insoluble carrier particles carrying neither a substance to be determined nor antibodies to the substance to an aqueous medium consisting essentially of a buffer having its buffer capacity in a neutral or alkaline region except for a carbonate-based buffer and a carbonic acid compound releasing a bicarbonate ion;
   2) keeping the suspension of step 1);
   3) reacting the suspension comprising the insoluble carrier particles with a sample comprising substance to be determined;
   4) adding a reagent comprising antibodies reactive with the substance to be determined to the mixture of step 3); and
   5) measuring agglutination of insoluble carrier particles formed in step 4).

2. The immunoassay according to claim 1, wherein the substance to be determined is hemoglobin A1c.

3. The immunoassay according to claim 1, wherein the carbonic acid compound releasing a bicarbonate ion is an alkali metal compound.

4. The immunoassay according to claim 1, wherein the concentration of the bicarbonate ion is 0.05 to 500 mmol/L.

5. The immunoassay according to claim 1, wherein the concentration of the buffer having its buffer capacity in a neutral or alkaline region is 0.1 to 500 mmol/L.

6. The immunoassay according to claim 1, wherein the insoluble carrier particles are latex.

* * * * *

UNITED STATES PATENT AND TRADEMARK OFFICE
CERTIFICATE OF CORRECTION

PATENT NO. : 8,431,415 B2
APPLICATION NO. : 12/509895
DATED : April 30, 2013
INVENTOR(S) : Kayoko Shigenobu It is certified that error appears in the above-identified patent and that said Letters Patent is hereby corrected as shown below:

On the Title page item (73), should read:

--Assignees: Kyowa Medex Co., Ltd., Toyko (JP), TFB Inc., Tokyo, (JP)--

Signed and Sealed this
Twentieth Day of August, 2013

Teresa Stanek Rea
*Acting Director of the United States Patent and Trademark Office*